(12) United States Patent
Chang et al.

(10) Patent No.: US 11,229,922 B2
(45) Date of Patent: Jan. 25, 2022

(54) PORTABLE HYDROGEN-CONTAINING OZONE WATER HUMIDIFIER

(71) Applicant: BGT MATERIALS LIMITED, Manchester (GB)

(72) Inventors: Kuo-Hsin Chang, Chiayi County (TW); Chung-Ping Lai, Hsinchu County (TW)

(73) Assignee: BGT MATERIALS LIMITED, Manchester (GB)

(*) Notice: Subject to any disclaimer, the term of this patent is extended or adjusted under 35 U.S.C. 154(b) by 44 days.

(21) Appl. No.: 16/908,413

(22) Filed: Jun. 22, 2020

(65) Prior Publication Data

US 2021/0394223 A1 Dec. 23, 2021

(51) Int. Cl.
| | |
|---|---|
| *C25B 1/04* | (2021.01) |
| *C25B 9/00* | (2021.01) |
| *B05B 17/06* | (2006.01) |
| *C02F 1/461* | (2006.01) |
| *C02F 103/02* | (2006.01) |

(52) U.S. Cl.
CPC ...... *B05B 17/0653* (2013.01); *C02F 1/46104* (2013.01); *C02F 2103/02* (2013.01); *C02F 2201/004* (2013.01); *C02F 2201/4611* (2013.01); *C02F 2201/4618* (2013.01); *C02F 2201/46125* (2013.01); *C02F 2201/46165* (2013.01)

(58) Field of Classification Search
CPC .. C25B 1/04; C25B 9/00; C25B 15/00; C25B 15/02; C25B 1/02; C25B 1/00; C25B 9/17; C25B 9/65; C25B 15/08
See application file for complete search history.

(56) References Cited

U.S. PATENT DOCUMENTS

| | | | |
|---|---|---|---|
| 2018/0228995 A1* | 8/2018 | Lin | ............................ C25B 1/04 |
| 2019/0062934 A1* | 2/2019 | Lin | ......................... A61M 11/00 |

FOREIGN PATENT DOCUMENTS

| | | |
|---|---|---|
| CN | 1317344 Y | 10/2001 |
| CN | 201006030 Y | 1/2008 |

* cited by examiner

*Primary Examiner* — Zulmariam Mendez
(74) *Attorney, Agent, or Firm* — Chun-Ming Shih; Lanway IPR Services

(57) ABSTRACT

A portable hydrogen-containing ozone water humidifier including a housing with a mist outlet, a water tank for storing water, a hydrogen-containing ozone water generator, an ultrasonic atomizer for converting water into mist, a rechargeable battery and an electronic controller is revealed. An outlet pipe is connected to the bottom of the water tank and the hydrogen-containing ozone water generator is disposed on the outlet pipe for hydrolysis of the water to generate oxygen and ozone gas at an anode plate and hydrogen gas at a cathode plate and further get disinfectant water formed by ozone water mixed with hydrogen-rich water while the ultrasonic atomizer is arranged at an outlet end of the outlet pipe. The rechargeable battery provides power to the electronic controller, the hydrogen-containing ozone water generator, and the ultrasonic atomizer for driving them to work. The humidifier is compact and easy to carry.

8 Claims, 7 Drawing Sheets

PORTABLE HYDROGEN-CONTAINING OZONE WATER HUMIDIFIER

BACKGROUND OF THE INVENTION

Technical Field

Figure 1:
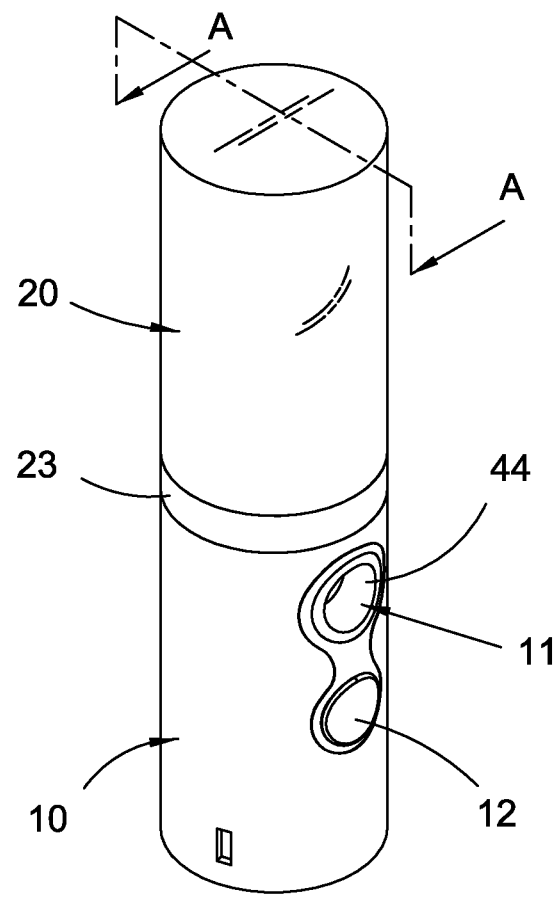
Figure 2:
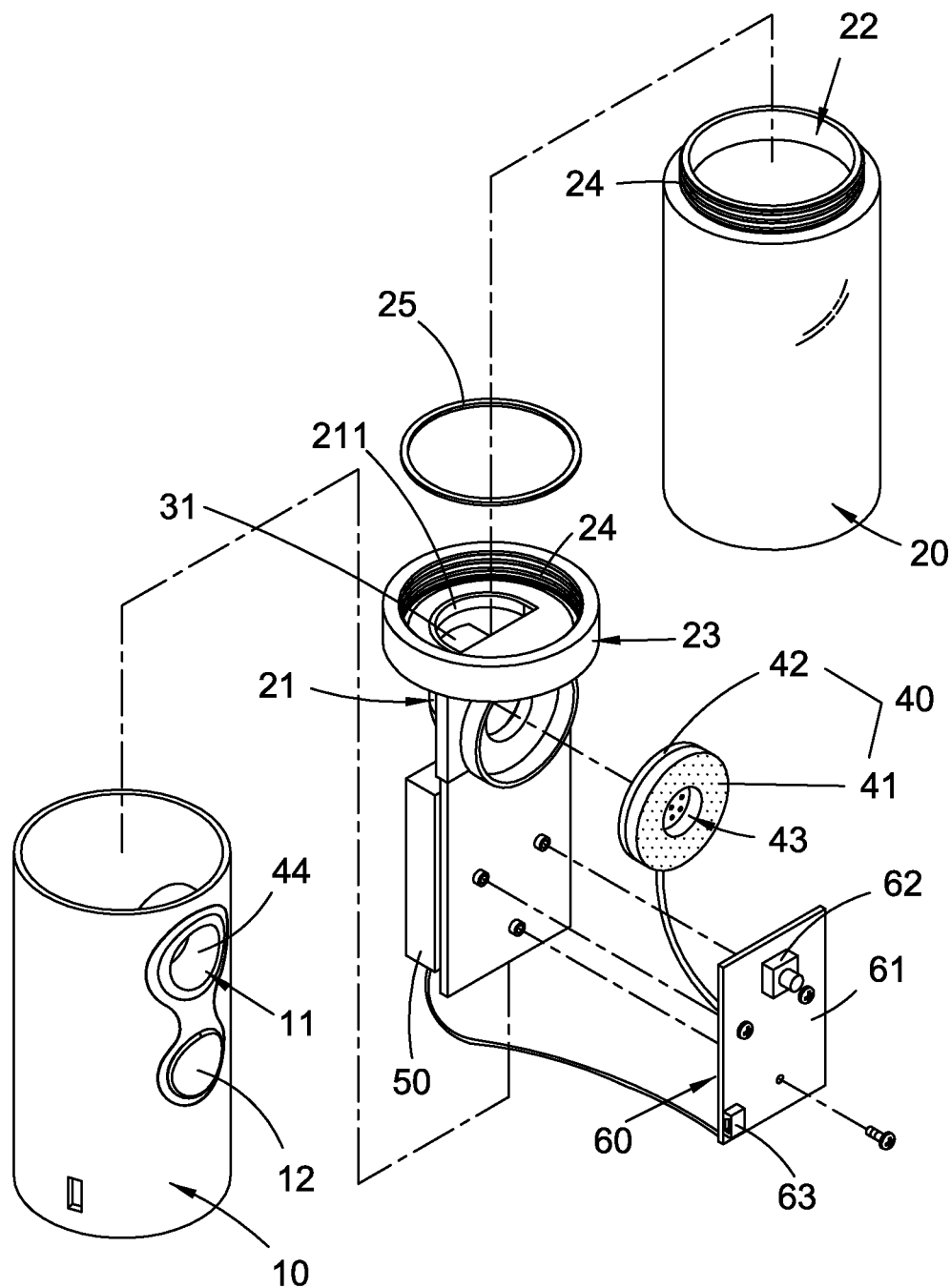

The present invention relates to an air humidifier, especially to a portable hydrogen-containing ozone water humidifier with humidification, disinfection and air purification functions.

Description of Related Art

Ozone is a strong oxidant and disinfectant with good ability in disinfection and degradation of organic contaminants. The disinfection effect of ozone on waste water is enhanced by being used in combination with ultrasonic waves, as revealed in the research by HE, Shi-Chuan, ZHU, Chang-Ping, SHAN, Ming-Lei, & FENG, Ruo (2005.09), "Recent advances in wastewater treatment with ultrasonic-ozone method", Journal of Technical Acoustics, Vol. 24, No. 3.

Ozone can be produced via UV (ultraviolet) light, corona discharge (electrical discharge), or electrolysis. The most common ways are corona discharge (electrical discharge) and electrolytic ozone production. The corona discharge method produces gas mixture containing ozone (not pure ozone) and toxic nitrogen oxides. There are two types of corona discharge ozone generators: the parallel-plate type and the shell and tube type. The parallel-plate type generates a greater amount of ozone than the shell and tube type. In recent years, electrolytic ozone production is widely used in ozone generators with hydrogen gas evolved in the cathode and oxygen gas evolved in the anode. The electrolytic ozone generator creates ozone with high concentration and no poisonous nitrogen oxides byproducts. Thus the electrolytic ozone generation technology has wide and promising applications.

The disinfection technology that combines ozone and ultrasonic waves has already been provided. Air is passed through an ozone generator to create ozone gas and then ozone gas is introduced into water to get ozone water. Next the ozone water is treated by ultrasonic atomization or spray head atomization for being applied to disinfection. Refer to Chinese Invention Pat. (Pub. No. CN1317344A), "disinfection method combining ultrasonic waves with ozone and device of the same", and Chinese Utility Model Patent with the number of announcement of grant of patent right CN201006030 "ultrasonic atomized ozone disinfector", both reveal similar techniques. Although these devices can provide disinfection by an ozone water mist, these devices have large volume which adversely affects mobility and portability.

SUMMARY OF THE INVENTION

Therefore it is a primary object of the present invention to provide a portable hydrogen-containing ozone water humidifier with humidification, disinfection and air purification functions.

In order to achieve the above object, a portable hydrogen-containing ozone water humidifier according to the present invention includes a housing, a water tank, a hydrogen-containing ozone water generator, an ultrasonic atomizer, a rechargeable battery and an electronic controller.

The housing is provided with a mist outlet on a front side. The water tank is disposed on the top of the housing and used for storing water while an outlet pipe is connected to the bottom of the water tank and mounted in the housing. An inlet end of the outlet pipe is connected to the inside of the water tank.

The hydrogen-containing ozone water generator includes an anode plate and a cathode plate, both being mounted in the water tank for electrolysis of water in the water tank. Thus oxygen and ozone gas are produced at the anode plate and hydrogen gas is generated at the cathode plate to get hydrogen-containing ozone water formed by mixing of ozone water and hydrogen-rich water.

The ultrasonic atomizer is arranged at the outlet end of the outlet pipe. An outlet port of the ultrasonic atomizer is connected to the mist outlet. The hydrogen-containing ozone water is converted into a hydrogen-containing ozone water mist by the ultrasonic atomizer and then passed through the mist outlet to be sprayed out.

The rechargeable battery is mounted in the housing.

The electronic controller which includes a control circuit, a power on/off switch and an electrical connector is mounted in the housing. The control circuit is electrically connected to the power on/off switch, the electrical connector, the rechargeable battery, the anode plate and the cathode plate of the electrolytic hydrogen-containing ozone water generator, and the ultrasonic atomizer. The control circuit can be electrically connected to an external power source by the electrical connector for charging the rechargeable battery. The rechargeable battery provides power to the control circuit, the hydrogen-containing ozone water generator and the ultrasonic atomizer while the power on/off switch is used to turn on/or off the control circuit, the hydrogen-containing ozone water generator, and the ultrasonic atomizer.

Preferably, the housing is a hollow tube and one end of the water tank is provided with an opening while an inlet end of the outlet pipe is connected to a tank cap. The tank cap is fixed on the top of the housing and is able to be either connected to or separated from the opening of the water tank.

Preferably, a thread and a sealing gasket are arranged at a connection between the opening and the tank cap of the water tank.

Preferably, a filling opening and an upper cover for closing the filling opening are disposed on the other end of the water tank, opposite to the end with the opening.

Preferably, the filling opening and the upper cover can be arranged at the top of the water tank. The water tank and the outlet pipe can be made by plastic injection molding and integrated into one part.

Preferably, the anode plate and the cathode plate are mounted in the outlet pipe.

Preferably, the ultrasonic atomizer consists of a piezoelectric ceramic plate and a micro-hole perforated metal sheet which is attached to a ring-shaped piezoelectric ceramic plate to form a composite. The micro-hole perforated metal sheet has micro holes aligned with a central hole of the piezoelectric ceramic plate and the central hole is used as the outlet port of the ultrasonic atomizer.

Preferably, a tapered tube is disposed on the outlet port of the ultrasonic atomizer. The tapered tube which has an entrance and an exit is tapered from the exit to the entrance. The outlet port of the ultrasonic atomizer is connected to the entrance of the tapered tube while the exit of the tapered tube is connected to the mist outlet.

Figure 3:
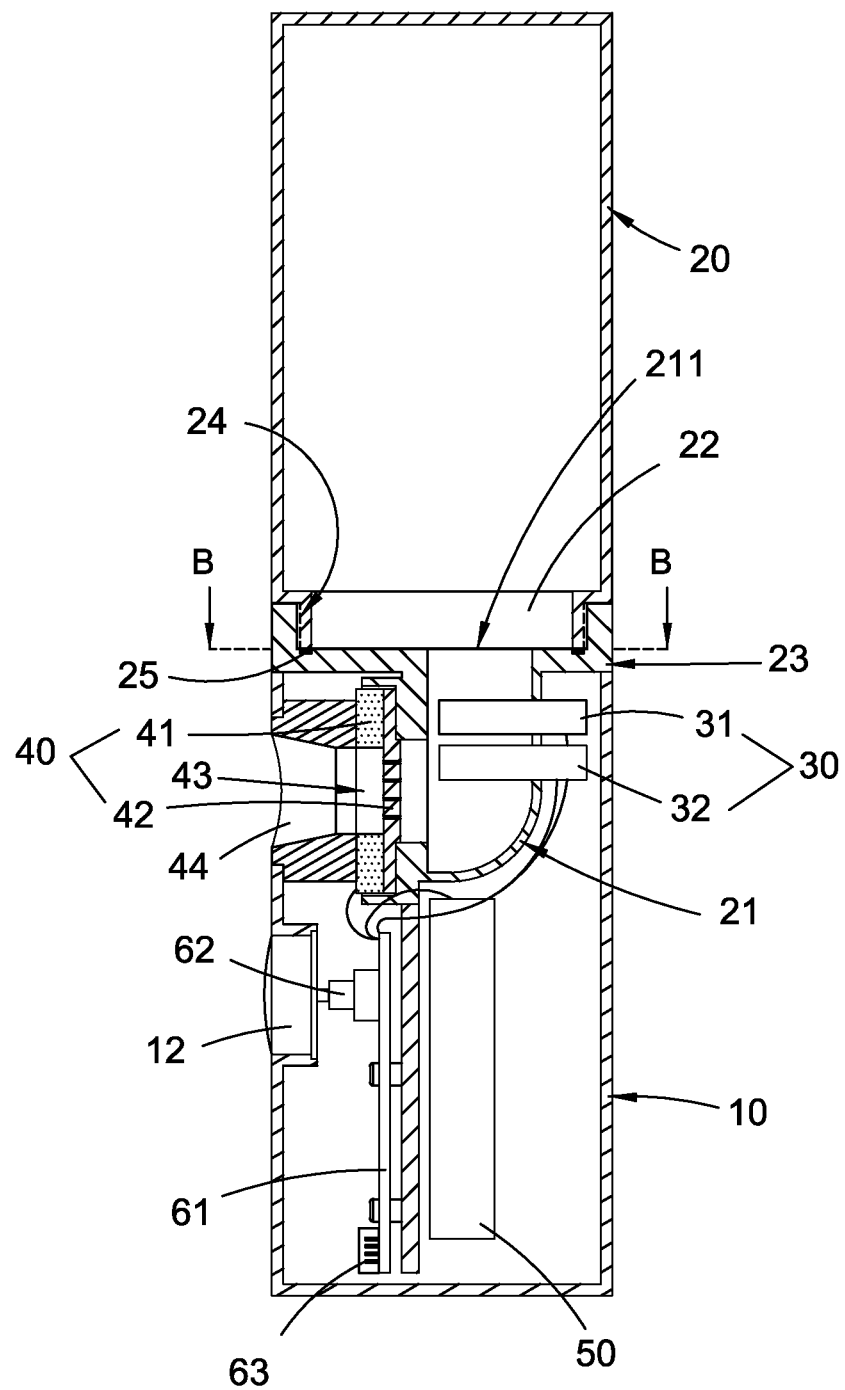
Figure 4:
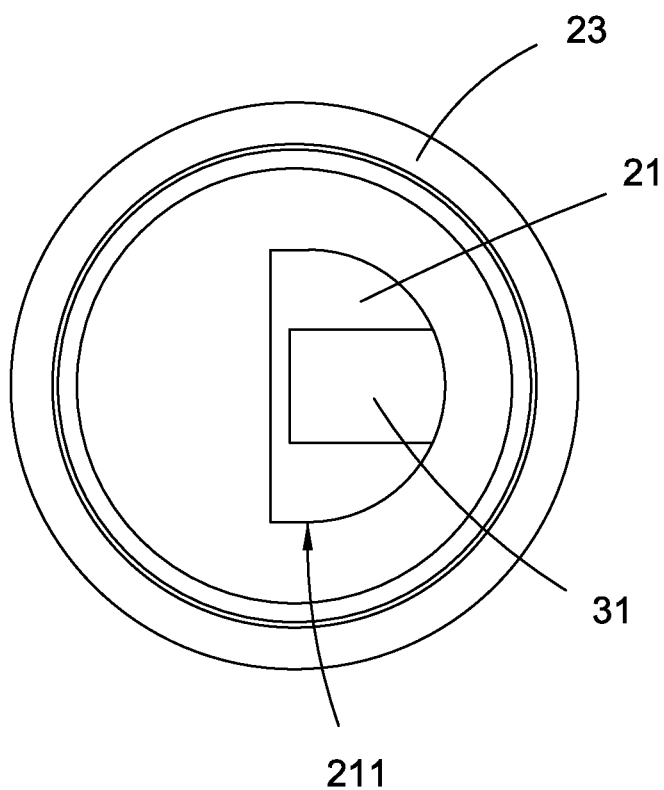
Figure 5:
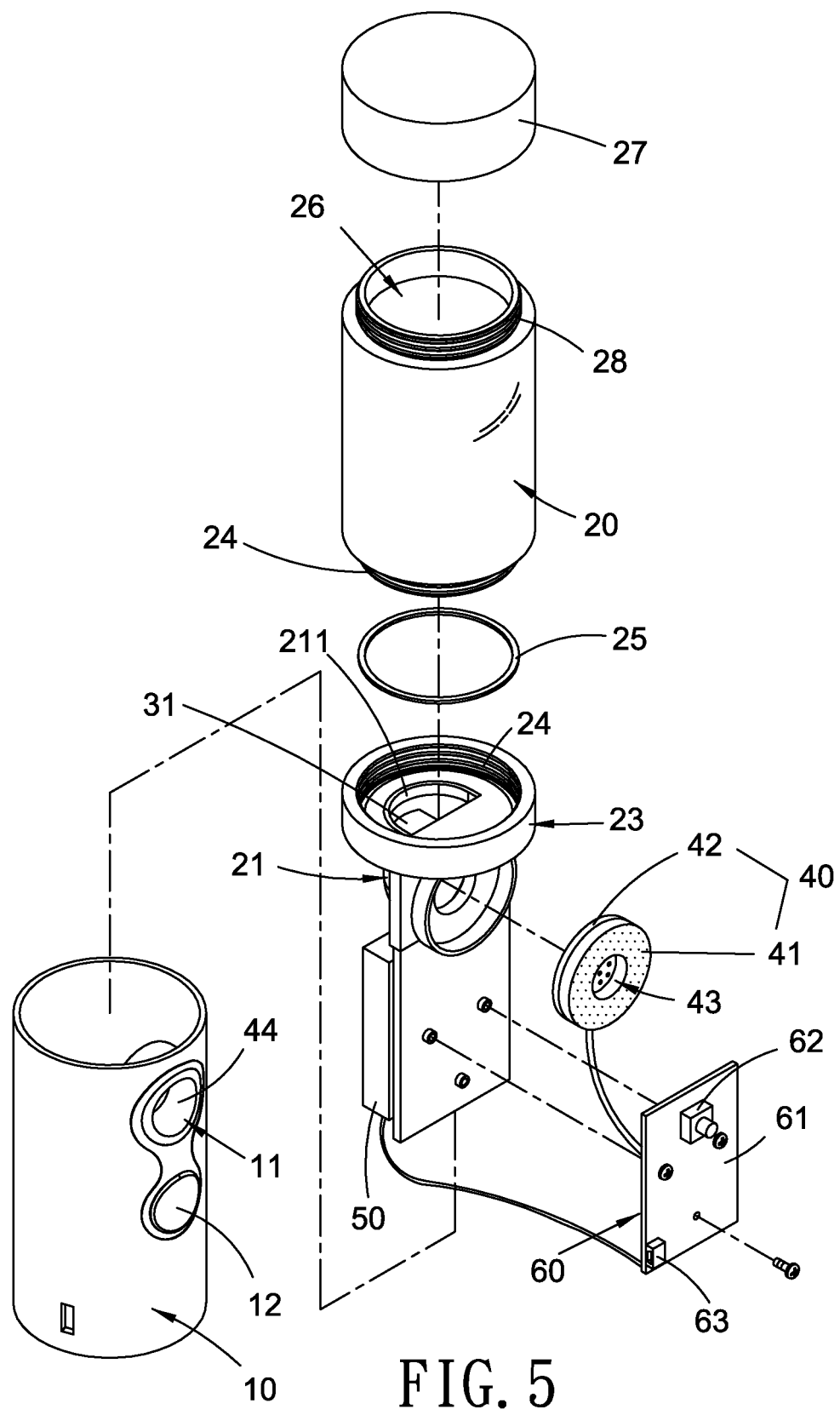
Figure 6:
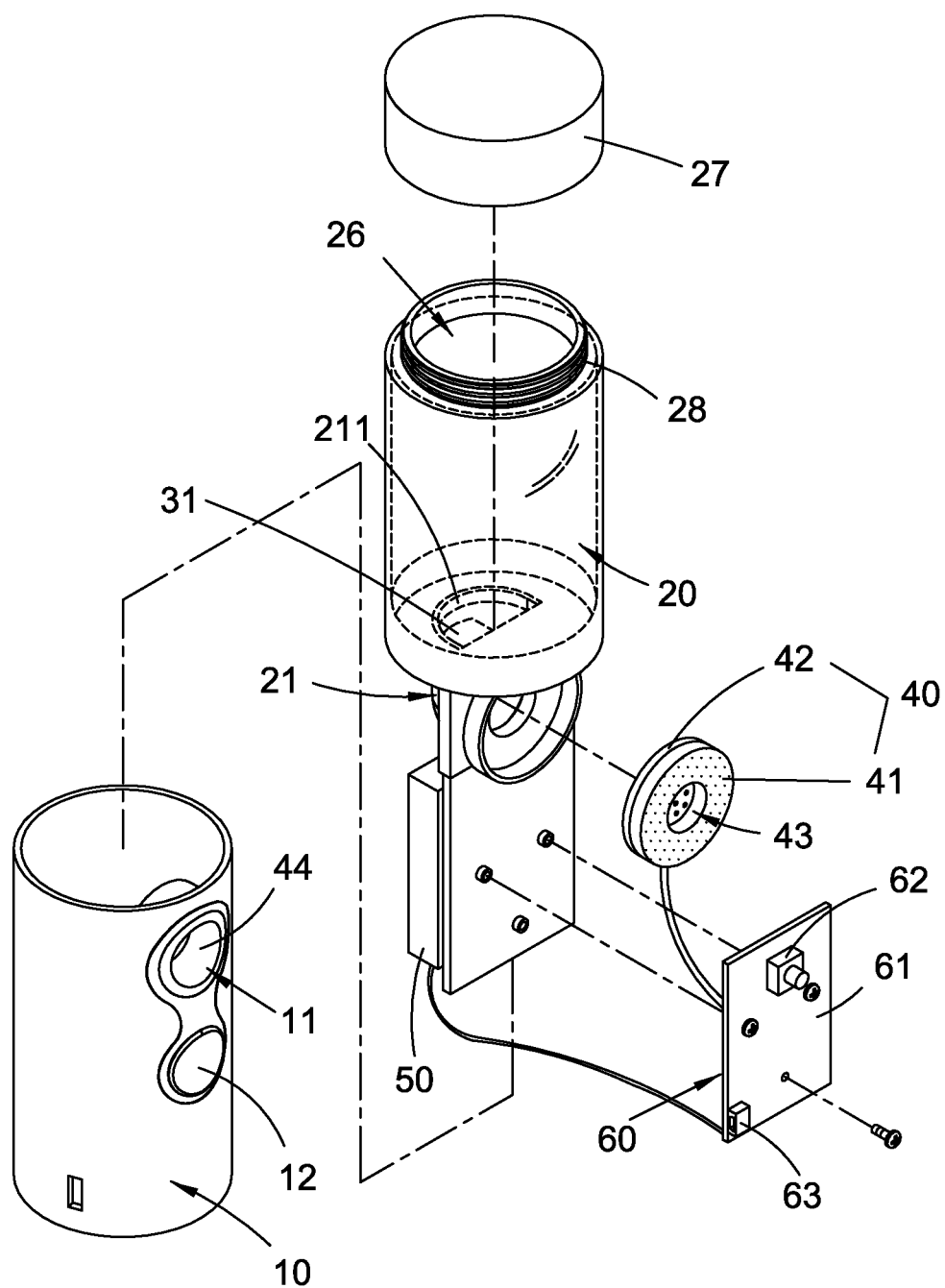
Figure 7:
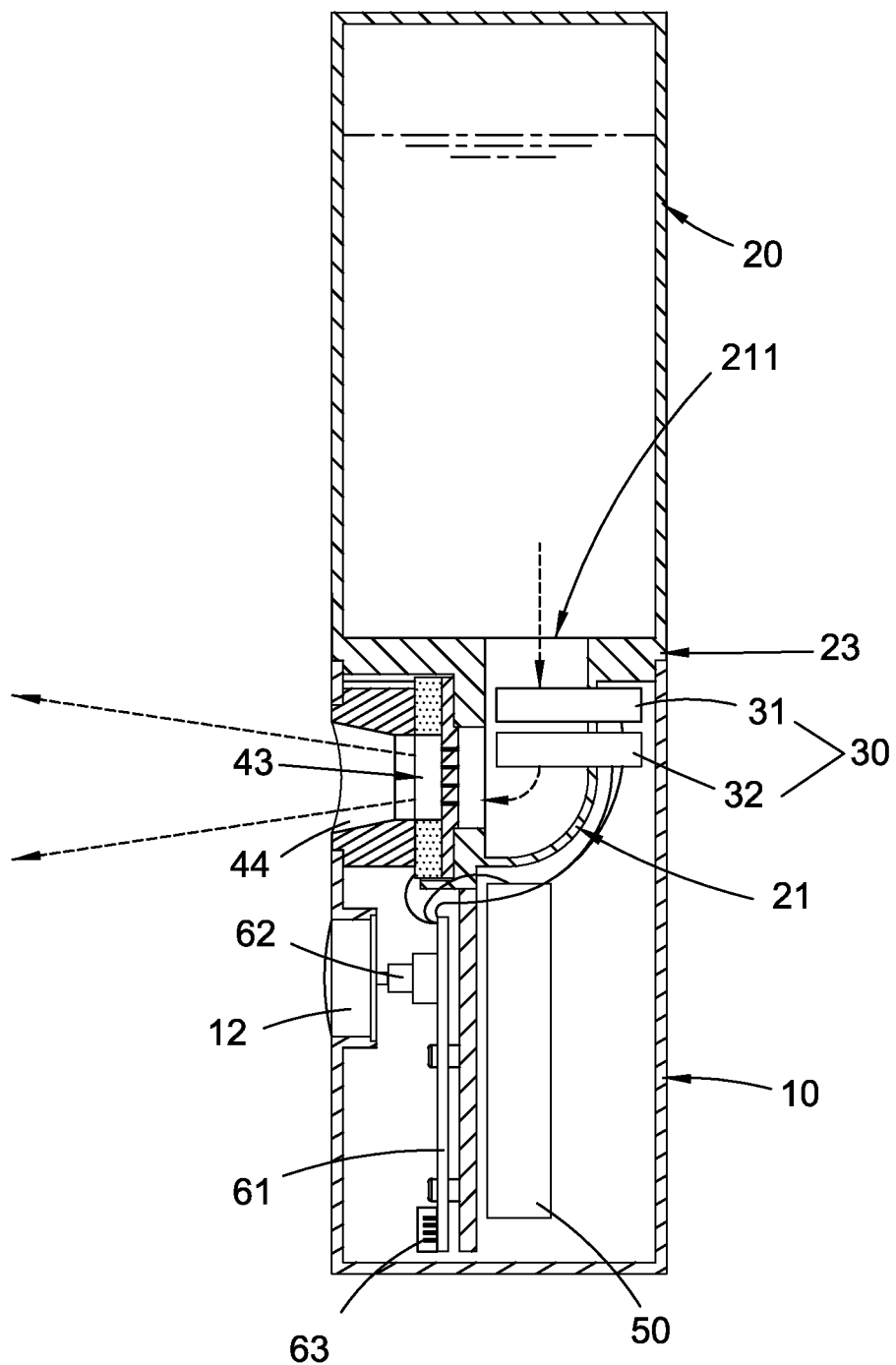

The portable hydrogen-containing ozone water humidifier of the present invention features on humidification, disinfection and air purification functions. The hydrogen-containing ozone water is atomized into the water mist by the micro-hole perforated metal sheet of the ultrasonic atomizer and the water mist interacts better with dirty air to improve disinfection and cleaning effect of the ozone water on the dirty air. The water mist is able to be sprayed out a further distance. Once the hydrogen-containing ozone water is absorbed by human bodies, ozone water provides disinfection effect on virus and bacteria while hydrogen-rich water reduces not only inflammation in human bodies but also the harm to the bodies caused by ozone water. The present portable hydrogen-containing ozone water humidifier has a simple structure and an upright style with the water tank arranged at the top of the housing. The portable hydrogen-containing ozone water humidifier is compact in volume, rechargeable and easy to carry.

The embodiments, advantages and functions of the present invention are described as follows with reference to the figures.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

FIG. 1 is a perspective view of an embodiment according to the present invention;

FIG. 2 is an explosive view of the embodiment in FIG. 1 according to the present invention;

FIG. 3 is a sectional view taken along line A-A shown in FIG. 1 according to the present invention;

FIG. 4 is a sectional view taken along line B-B shown in FIG. 3 according to the present invention;

FIG. 5 is an explosive view of another embodiment according to the present invention;

FIG. 6 is an explosive view of a further embodiment showing a water tank and an outlet pipe according to the present invention;

FIG. 7 is a schematic drawing showing an action of an embodiment according to the present invention.

DETAILED DESCRIPTION OF THE PREFERRED EMBODIMENT

The relative positions descried in the following embodiments, including upper, lower, left and right, unless otherwise specified, are based on the directions indicated by the components in the figures.

Refer to FIG. 1 and FIG. 2, a perspective view and an explosive view of a portable hydrogen-containing ozone water humidifier according to the present invention are revealed. The portable hydrogen-containing ozone water humidifier includes a housing 10, a water tank 20, a hydrogen-containing ozone water generator 30, an ultrasonic atomizer 40, a rechargeable battery 50 and an electronic controller 60. The housing 10 is a hollow tube provided with a mist outlet 11 on a front side while the hydrogen-containing ozone water generator 30, the ultrasonic atomizer 40, the rechargeable battery 50 and the electronic controller 60 are all mounted in the housing 10. The rechargeable battery 50 is preferably a lithium-ion battery. The present portable hydrogen-containing ozone water humidifier is designed in an upright style and the water tank 20 is arranged at the top of the housing 10. The portable hydrogen-containing ozone water humidifier is compact in volume, rechargeable and easy to carry.

The water tank 20 is for storing water while an outlet pipe 21 is connected to the bottom of the water tank 20 and enclosed in the housing 10. An inlet end 211 of the outlet pipe 21 is connected to the inside of the water tank 20. In a preferred embodiment, the water tank 20 is made from transparent materials such as plastic so that the amount of the water in the water tank 20 can be observed visually. Moreover, the water in the water tank 20 can be added with antimicrobial additives or essences to provide functions of disinfection, humidification and aroma.

As shown in FIG. 2, the water tank 20 is a bottle with an opening 22 on one end. The inlet end 211 on top of the outlet pipe 21 is connected with a tank cap 23. The outlet pipe 21 and the tank cap 23 can be made by plastic injection molding and integrated into one part. The tank cap 23 is fixed on the top of the housing 10 (such as by adhesion or ultrasonic welding). The tank cap 23 can be either connected to or separated from the opening 22 of the water tank 20. For example, a thread 24 and a sealing gasket 25 are arranged at a connection between the opening 22 and the tank cap 23 of the water tank 20. The tank cap 23 can be connected or disconnected to the opening 22 of the water tank 20 by the thread 24. Before use, water is filled into the water tank 20 through the opening 22 firstly. Then the tank cap 23 on the top of the housing 10 is connected to the opening 22 of the water tank 20. Next the opening 22 of the water tank 20 is facing downward to make water flow out through the outlet pipe 21 (as shown in FIG. 3 and FIG. 4). Now the portable hydrogen-containing ozone water humidifier can be used by the bottom of the housing 10 being placed or set on a table surface or other planes.

Refer to FIG. 5, another embodiment of the water tank 20 is revealed. The difference between this water tank 20 and the one shown in FIG. 2 is in that the water tank 20 shown in FIG. 5 includes the opening 22, the sealing gasket 25, a filling opening 26 on the other end thereof opposite to the end with the opening 22, and an upper cover 27 used for closing the filling opening 26 and located on the other end thereof opposite to the end with the opening 22. In a preferred embodiment, a thread 28 is disposed on a connection between the filling opening 26 and the upper cover 27. After the opening 22 of the water tank 20 being connected to the tank cap 23 on the top of the housing 10, water is filled into the water tank 20 through the filling opening 26. In other embodiments, the filling opening 26 is sealed by a plug instead of the upper cover 27.

Refer to FIG. 6, a further embodiment of the water tank 20 is disclosed. The water tank 20 and a mist structure thereunder can be made by plastic injection molding and integrated into one part. The mist structure consists of an outlet pipe 21 and a tank cap 23 while a filling opening 26 and an upper cover 27 are still located at the top of the water tank 20. Basically, the tank cap 23 can be considered as the inlet end 211 of the outlet pipe 21. That means the water tank 20 and the outlet pipe 21 can be made by plastic injection molding and integrated into one part. The sectional view of the one part is shown in FIG. 7. Compared with the embodiments shown in FIG. 1 and FIG. 5, the water tank 20 and the outlet pipe 21 in the embodiment shown in FIG. 6 has the simpler structure due to integration of them by plastic injection molding. There is no need to use a sealing gasket 25 so that the assembly cost is further decreased.

The hydrogen-containing ozone water generator 30 is an electrolytic hydrogen-containing ozone water generator 30 composed of an anode plate 31 and a cathode plate 32. The anode plate 31 and the cathode plate 32 are mounted in the water tank 20 for electrolysis of water in the water tank 20 to generate oxygen and ozone gas at the anode plate 31 and hydrogen gas at the cathode plate 32. Thereby disinfectant water formed by ozone water mixed with hydrogen-rich water is obtained. The anode plate 31 and the cathode plate 32 are electrically connected to electronic controller 60. The electronic controller 60 not only drives the hydrogen-containing ozone water generator 30 to work but also controls its operation time once a direct voltage/or current is applied to the anode plate 31 and the cathode plate 32. Nano-scale oxygen gas and ozone gas are produced by electrolysis of water at the anode plate 31 and ozone water is further generated. The shape of the anode plate 31 and the cathode plate 32 is not limited. For example, the anode plate 31 and the cathode plate 32 shown in the embodiment in FIG. 3 and FIG. 4 are only an exemplary configuration. The anode plate 31 and the cathode plate 32 can switch position as long as they are in close positions, their shapes are symmetrical, and the electric field generated by them is uniform. The shape of the anode plate 31 and the cathode plate 32 can be a column, a mesh, a sheet or other symmetrical shape.

In a preferred embodiment, the anode plate 31 and the cathode plate 32 are mounted in the outlet pipe 21. It should be noted that the size of the anode plate 31 and the cathode plate 32 should not block the outlet pipe 21. That means the total size of the anode plate 31 and the cathode plate 32 is not over the cross-sectional area of the outlet pipe 21. Water in the water tank 20 passes through the anode plate 31 and the cathode plate 32 while moving along the outlet pipe 21 to an outlet end of the outlet pipe 21. During electrolysis, water is oxidized at the anode plate 31 to get oxygen gas and ozone gas while hydrogen gas is generated at the cathode plate 32. Thereby disinfectant water formed by ozone water mixed with hydrogen-rich water is obtained.

Moreover, the anode plate 31 is preferably to be made of active electrode materials with anti-oxidative activity including platinum, stainless steel, titanium, insoluble anode materials (such as dimensionally stable anode (DSA)), graphite/or graphene, doped and undoped oxides (such as $RuO_2$, $IrO_2$, $PbO_2$, $SnO_2$, $TiO_2$, etc.), nitrogen-doped or boron-doped diamond, or their combinations. As to the cathode plate 32, it is preferably made of platinum, stainless steel, titanium, stainless steel with a coating that promotes hydrogen generation (such as platinum), titanium with a coating that promotes hydrogen generation (such as platinum), graphite/or graphene, or their combinations. In a preferred embodiment, the anode plate 31 includes a stainless steel electrode coated with the active electrode materials with anti-oxidative activity mentioned above, a titanium electrode coated with the active electrode materials with anti-oxidative activity mentioned above, a graphite electrode or a graphene electrode.

The ultrasonic atomizer 40 is arranged at the outlet end of the outlet pipe 21. For example, the ultrasonic atomizer 40 is adhered on the outlet end of the outlet pipe 21 by waterproof adhesive. The ultrasonic atomizer 40 basically consists of a piezoelectric ceramic plate 41, a micro-hole perforated metal sheet 42 attached to a ring-shaped piezoelectric ceramic plate 41 to form a composite, and an outlet port 43 which is a central hole of the piezoelectric ceramic plate 41. The micro-hole perforated metal sheet 42 has micro holes aligned with the outlet port 43 of the ultrasonic atomizer 40 while the outlet port 43 is connected to the mist outlet 11 so that the disinfectant water mentioned above is atomized into hydrogen-containing ozone water mist by the micro-hole perforated metal sheet 42 of the ultrasonic atomizer 40 and then passed through the micro holes and the mist outlet 11 to be sprayed out.

In a preferred embodiment, a tapered tube 44 (as shown in FIG. 3) is disposed on the outlet port 43 of the ultrasonic atomizer 40. The tapered tube 44 which has an entrance and an exit is tapered from the exit to the entrance. The outlet port 43 of the ultrasonic atomizer 40 is connected to the entrance of the tapered tube 44 while the exit of the tapered tube 44 is connected to the mist outlet 11. The hydrogen-containing ozone water mist is first passed through the tapered tube 44 and then sprayed out through the mist outlet 11 so that the hydrogen-containing ozone water mist is more concentrated and sprayed out a further distance, as shown in FIG. 7.

As shown in FIG. 2, FIG. 3, FIG. 6 and FIG. 7, the electronic controller 60 is electrically connected to the hydrogen-containing ozone water generator 30, the ultrasonic atomizer 40, and the rechargeable battery 50. The rechargeable battery 50 provides power to the electronic controller 60, the hydrogen-containing ozone water generator 30, and the ultrasonic atomizer 40. The electronic controller 60 consists of a control circuit 61, a power on/off switch 62 and an electrical connector 63. The control circuit 61 is electrically connected to the power on/off switch 62, the electrical connector 63, the rechargeable battery 50, the anode plate 31 and the cathode plate 32 of the electrolytic hydrogen-containing ozone water generator 30, and the piezoelectric ceramic plate 41 of the ultrasonic atomizer 40. In the housing 10, an insertion port of the electrical connector 63 is exposed while the control circuit 61 can be electrically connected to an external power source by the electrical connector 63 for charging the rechargeable battery 50. The control circuit 61 which gets power from the rechargeable battery 50 drives the hydrogen-containing ozone water generator 30 and the ultrasonic atomizer 40 to work and controls the operation time. The power on/off switch 62 can be a push-type electrical component. A button 12 is disposed on the front side of the housing 10 and a front surface of the button 12 is exposed. While in use, the button 12 is pressed for driving the power on/off switch 62 to turn on or turn off the control circuit 61, the hydrogen-containing ozone water generator 30, and the ultrasonic atomizer 40.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A portable hydrogen-containing ozone water humidifier comprising:

a housing provided with a mist outlet on a front side thereof;

a water tank disposed on the top of the housing for storing water and having an outlet pipe which is connected to the bottom of the water tank, mounted in the housing, and provided with an inlet end connected to the inside of the water tank;

a hydrogen-containing ozone water generator which includes an anode plate and a cathode plate, both being mounted in the water tank for electrolysis of water in the water tank to produce oxygen and ozone gas at the anode plate and hydrogen gas at the cathode plate, and further obtain hydrogen-containing ozone water formed by mixing of ozone water and hydrogen-rich water;

an ultrasonic atomizer which is arranged at an outlet end of the outlet pipe, having an outlet port connected to the mist outlet, and used for atomizing the hydrogen-containing ozone water into hydrogen-containing ozone water mist; the hydrogen-containing ozone water mist being passed through the mist outlet to be sprayed out;

a rechargeable battery mounted in the housing; and an electronic controller mounted in the housing and including a control circuit, a power on/off switch and an electrical connector; the control circuit electrically connected to the electrical connector, the power on/off switch, the rechargeable battery, the anode plate and the cathode plate of the electrolytic hydrogen-containing ozone water generator, and the ultrasonic atomizer; the control circuit able to be electrically connected to an external power source by the electrical connector for charging the rechargeable battery while the rechargeable battery providing power to the control circuit, the hydrogen-containing ozone water generator, and the ultrasonic atomizer; the power on/off switch used for turning on/or off the control circuit, the hydrogen-containing ozone water generator, and the ultrasonic atomizer.

2. The device as claimed in claim 1, wherein the housing is a hollow tube and one end of the water tank is provided with an opening while the inlet end of the outlet pipe is connected to a tank cap; wherein the tank cap is fixed on the top of the housing and is able to be either connected to or separated from the opening of the water tank.

3. The device as claimed in claim 2, wherein a thread and a sealing gasket are disposed on a connection between the opening and the tank cap of the water tank.

4. The device as claimed in claim 2, wherein a filling opening and an upper cover for closing the filling opening are disposed on the other end of the water tank, opposite to the end with the opening.

5. The device as claimed in claim 4, wherein the filling opening and the upper cover are able to be arranged at the top of the water tank; wherein the water tank and the outlet pipe are made by plastic injection molding and integrated into one part.

6. The device as claimed in claim 1, wherein the anode plate and the cathode plate are mounted in the outlet pipe.

7. The device as claimed in claim 1, wherein the ultrasonic atomizer includes a piezoelectric ceramic plate and a micro-hole perforated metal sheet which is attached to a ring-shaped piezoelectric ceramic plate to form a composite; the micro-hole perforated metal sheet has micro holes aligned with a central hole of the piezoelectric ceramic plate and the central hole is used as the outlet port of the ultrasonic atomizer.

8. The device as claimed in claim 1, wherein a tapered tube is disposed on the outlet port of the ultrasonic atomizer, including an entrance and an exit, and tapered from the exit to the entrance; wherein the outlet port of the ultrasonic atomizer is connected to the entrance of the tapered tube while the exit of the tapered tube is connected to the mist outlet.

* * * * *